(12) United States Patent
Salvadori et al.

(10) Patent No.: US 8,328,734 B2
(45) Date of Patent: Dec. 11, 2012

(54) URINE METER WITH IMPROVED DRAIN CONSTRUCTION

(75) Inventors: Lawrence Salvadori, San Diego, CA (US); Stephen Tully, Cambridge, MA (US)

(73) Assignee: Covidien LP, Mansfield, MA (US)

( * ) Notice: Subject to any disclaimer, the term of this patent is extended or adjusted under 35 U.S.C. 154(b) by 1562 days.

(21) Appl. No.: 11/362,659

(22) Filed: Feb. 24, 2006

(65) Prior Publication Data

US 2007/0213639 A1 Sep. 13, 2007

(51) Int. Cl.
 *A61B 5/00* (2006.01)
 *B65D 81/00* (2006.01)
 *A61M 1/00* (2006.01)

(52) U.S. Cl. ........ 600/575; 604/322; 604/323; 604/324; 604/325; 604/326

(58) Field of Classification Search .................. 600/575; 604/322–326

See application file for complete search history.

(56) References Cited

U.S. PATENT DOCUMENTS

| | | |
|---|---|---|
| 693,127 A | 2/1902 | Gardner et al. |
| 1,951,196 A | 3/1934 | Medows et al. |
| 2,630,303 A | 3/1953 | Krucker |
| 3,259,920 A | 7/1966 | Voller |
| 3,312,221 A | 4/1967 | Overment |
| 3,529,599 A | 9/1970 | Folkman et al. |
| 3,534,738 A | 10/1970 | Huck |
| 3,537,109 A | 11/1970 | Spurrier et al. |
| 3,537,455 A | 11/1970 | Skyles et al. |
| 3,583,401 A | 6/1971 | Vailiancourt |
| 3,601,119 A | 8/1971 | Engelsher |
| 3,650,272 A | 3/1972 | Ericson |
| 3,661,143 A | 5/1972 | Henkin |
| 3,661,153 A | 5/1972 | Polk et al. |
| 3,683,894 A | 8/1972 | Villari |
| 3,699,964 A | 10/1972 | Ericson |
| 3,716,055 A | 2/1973 | Schultze |
| 3,776,231 A | 12/1973 | Holbrook et al. |
| 3,800,795 A | 4/1974 | Walker |
| 3,820,546 A | 6/1974 | Chittenden et al. |

(Continued)

FOREIGN PATENT DOCUMENTS

EP 0 428 331 B1 5/1991

(Continued)

OTHER PUBLICATIONS

European Search Report for European Application No. 08168279.1, mailed on Oct. 1, 2009.

*Primary Examiner* — Sean Dougherty
(74) *Attorney, Agent, or Firm* — Lisa E. Winsor, Esq.

(57) ABSTRACT

A urine meter is provided for use in a urine collection system. The urine meter includes a housing defining at least one fluid receptacle and having a concave upper wall having first and second ends and a central portion of reduced height. The housing defines first and second drain openings positioned adjacent respect ends of the upper wall. The housing also defines an inlet port extending through the central portion of the upper wall. A drain tube having a discharge end is positioned through the inlet port to direct fluid into the fluid receptacle. The drain tube has an internal surface having substantially no discontinuities. In one embodiment, the housing defines a centrally located first fluid receptacle and a second fluid receptacle which is positioned about the first fluid receptacle.

14 Claims, 9 Drawing Sheets

U.S. PATENT DOCUMENTS

| | | | |
|---|---|---|---|
| 3,831,453 A | 8/1974 | McWhorter | |
| 3,838,691 A | 10/1974 | Paludan et al. | |
| 3,888,236 A | 6/1975 | Marx | |
| 3,896,718 A | 7/1975 | Giambalvo | |
| 3,906,935 A | 9/1975 | Raia et al. | |
| 3,943,929 A | 3/1976 | Patel | |
| 3,952,729 A | 4/1976 | Libman et al. | |
| 3,961,529 A * | 6/1976 | Hanifl | 600/575 |
| 4,000,649 A * | 1/1977 | Hanifl | 600/575 |
| 4,002,075 A | 1/1977 | Cross | |
| 4,013,064 A | 3/1977 | Patel et al. | |
| 4,014,322 A | 3/1977 | Shah | |
| 4,015,605 A | 4/1977 | McWhorter | |
| 4,019,707 A | 4/1977 | Quinn et al. | |
| 4,027,842 A | 6/1977 | Mittleman | |
| 4,055,187 A | 10/1977 | Patel et al. | |
| 4,085,616 A | 4/1978 | Patel et al. | |
| 4,085,755 A | 4/1978 | Burrage | |
| 4,095,589 A * | 6/1978 | Manschot et al. | 600/575 |
| 4,100,802 A | 7/1978 | Layton | |
| 4,105,500 A | 8/1978 | Libman et al. | |
| 4,106,675 A | 8/1978 | Taylor | |
| 4,109,530 A | 8/1978 | Kim | |
| 4,109,837 A | 8/1978 | Taylor | |
| 4,131,016 A | 12/1978 | Layton | |
| 4,176,412 A | 12/1979 | Peterson | |
| 4,178,934 A | 12/1979 | Forman | |
| 4,187,722 A | 2/1980 | Layton | |
| 4,189,789 A | 2/1980 | Hofstetter | |
| 4,192,295 A | 3/1980 | Sherlock | |
| 4,200,112 A | 4/1980 | McWhorter | |
| 4,219,177 A | 8/1980 | O'Day | |
| 4,238,448 A | 12/1980 | Salvadori et al. | |
| 4,241,017 A | 12/1980 | Balistreri | |
| 4,254,771 A | 3/1981 | Vidal | |
| 4,265,243 A | 5/1981 | Taylor | |
| 4,280,498 A | 7/1981 | Jensen | |
| 4,301,813 A | 11/1981 | Merry et al. | |
| 4,305,290 A * | 12/1981 | Taylor | 73/427 |
| 4,305,403 A | 12/1981 | Dunn | |
| 4,305,404 A | 12/1981 | Dunn | |
| 4,305,405 A * | 12/1981 | Meisch | 600/575 |
| 4,312,351 A | 1/1982 | Kurtz et al. | |
| 4,312,352 A | 1/1982 | Meisch et al. | |
| 4,313,447 A | 2/1982 | Peterson et al. | |
| 4,317,550 A | 3/1982 | Hannah | |
| 4,328,828 A | 5/1982 | Cianci | |
| 4,332,252 A | 6/1982 | Taylor | |
| 4,333,480 A | 6/1982 | Villari et al. | |
| 4,334,537 A | 6/1982 | Peterson | |
| 4,344,432 A | 8/1982 | Pankau | |
| 4,366,836 A | 1/1983 | Villari | |
| 4,372,313 A | 2/1983 | Villari et al. | |
| 4,384,485 A | 5/1983 | Layton et al. | |
| 4,386,930 A | 6/1983 | Cianci | |
| 4,393,880 A | 7/1983 | Taylor | |
| 4,417,891 A | 11/1983 | Cianci | |
| 4,417,892 A | 11/1983 | Meisch | |
| 4,421,509 A | 12/1983 | Schneider et al. | |
| 4,432,763 A * | 2/1984 | Manschot et al. | 604/262 |
| 4,436,024 A | 3/1984 | Arden et al. | |
| 4,447,939 A | 5/1984 | Taylor | |
| 4,448,207 A * | 5/1984 | Parrish | 600/584 |
| 4,449,969 A | 5/1984 | Schweizer | |
| 4,450,936 A | 5/1984 | Strom | |
| 4,452,253 A | 6/1984 | Peterson et al. | |
| 4,460,362 A | 7/1984 | Bates | |
| 4,462,510 A | 7/1984 | Steer et al. | |
| 4,465,479 A | 8/1984 | Meisch | |
| 4,465,484 A | 8/1984 | Cianci | |
| 4,475,907 A | 10/1984 | Voges | |
| 4,483,688 A | 11/1984 | Akiyama | |
| 4,490,144 A | 12/1984 | Steigerwald | |
| 4,501,584 A | 2/1985 | Cianci et al. | |
| 4,503,864 A | 3/1985 | Powers | |
| 4,511,357 A | 4/1985 | Steigerwald | |
| 4,511,358 A | 4/1985 | Johnson, Jr. et al. | |
| 4,512,770 A | 4/1985 | Cianci et al. | |
| 4,521,213 A | 6/1985 | Steigerwald | |
| 4,526,576 A | 7/1985 | Cianci | |
| 4,529,398 A | 7/1985 | Wong et al. | |
| 4,534,766 A | 8/1985 | Steer et al. | |
| 4,551,141 A | 11/1985 | McNeil | |
| 4,562,984 A | 1/1986 | Sherlock et al. | |
| 4,564,361 A | 1/1986 | Akiyama | |
| 4,573,983 A | 3/1986 | Annis | |
| 4,579,126 A * | 4/1986 | Cianci | 600/580 |
| 4,581,763 A | 4/1986 | Olsen | |
| 4,604,092 A | 8/1986 | Silver | |
| 4,604,095 A | 8/1986 | Samuelsen | |
| 4,606,420 A | 8/1986 | Silver | |
| 4,606,736 A | 8/1986 | Van De Weghe | |
| 4,619,648 A | 10/1986 | Rath et al. | |
| 4,622,981 A | 11/1986 | Sherlock | |
| 4,625,734 A | 12/1986 | Sherlock et al. | |
| 4,631,056 A | 12/1986 | Dye | |
| 4,633,887 A | 1/1987 | Edwards et al. | |
| 4,634,437 A | 1/1987 | Lowthian | |
| 4,640,128 A | 2/1987 | Lewis | |
| 4,642,105 A | 2/1987 | Toter | |
| 4,650,478 A | 3/1987 | Dunn | |
| 4,658,834 A | 4/1987 | Blankenship et al. | |
| 4,659,329 A | 4/1987 | Annis | |
| 4,661,100 A | 4/1987 | Rechsteiner | |
| 4,691,557 A | 9/1987 | Dunn et al. | |
| 4,693,707 A | 9/1987 | Dye | |
| 4,693,712 A | 9/1987 | Bates | |
| 4,699,155 A | 10/1987 | Villari et al. | |
| 4,700,714 A | 10/1987 | Fuisz | |
| 4,702,740 A | 10/1987 | Bates | |
| 4,712,567 A | 12/1987 | Gille | |
| 4,717,388 A | 1/1988 | Steer et al. | |
| 4,723,944 A * | 2/1988 | Jensen | 604/323 |
| 4,723,950 A | 2/1988 | Lee | |
| 4,728,324 A | 3/1988 | Steigerwald et al. | |
| 4,731,062 A | 3/1988 | Gross et al. | |
| 4,738,671 A | 4/1988 | Elliott et al. | |
| 4,743,236 A * | 5/1988 | Manschot | 604/323 |
| 4,745,929 A | 5/1988 | Silver | |
| 4,753,249 A | 6/1988 | Muller | |
| 4,790,837 A | 12/1988 | Gross et al. | |
| 4,804,376 A | 2/1989 | Layton | |
| 4,815,477 A | 3/1989 | McWhorter et al. | |
| 4,838,876 A | 6/1989 | Wong et al. | |
| 4,850,375 A | 7/1989 | Rosenberg | |
| D303,714 S | 9/1989 | Manschot | |
| 4,865,046 A | 9/1989 | Duran | |
| 4,909,478 A | 3/1990 | Steer | |
| 4,911,697 A | 3/1990 | Kerwin | |
| 4,913,161 A | 4/1990 | Villari et al. | |
| 4,936,837 A | 6/1990 | Wexler et al. | |
| 4,946,451 A | 8/1990 | Cianci | |
| 4,955,879 A | 9/1990 | Mervine | |
| 4,972,844 A | 11/1990 | Cianci et al. | |
| 5,026,359 A | 6/1991 | Burroughs | |
| 5,098,418 A | 3/1992 | Maitz et al. | |
| 5,116,139 A | 5/1992 | Young et al. | |
| 5,119,675 A * | 6/1992 | Mohiuddin | 73/223 |
| 5,160,329 A | 11/1992 | Oxley | |
| 5,207,661 A | 5/1993 | Repschlager | |
| 5,211,642 A | 5/1993 | Clendenning | |
| 5,217,443 A | 6/1993 | Oxley | |
| 5,300,050 A | 4/1994 | Everett, Jr. et al. | |
| 5,312,379 A | 5/1994 | Rahe | |
| 5,354,132 A | 10/1994 | Young et al. | |
| 5,356,398 A | 10/1994 | Willis | |
| 5,368,583 A | 11/1994 | Fleury | |
| 5,409,014 A * | 4/1995 | Napoli et al. | 600/575 |
| 5,417,657 A | 5/1995 | Hauer | |
| 5,423,792 A | 6/1995 | Oxley | |
| 5,429,624 A | 7/1995 | Coelho, Jr. | |
| 5,439,456 A | 8/1995 | Fabricant | |
| 5,466,229 A | 11/1995 | Elson et al. | |
| 5,489,281 A | 2/1996 | Watanabe et al. | |
| 5,507,734 A | 4/1996 | Everett, Jr. et al. | |
| 5,523,055 A | 6/1996 | Hansen et al. | |
| 5,569,225 A | 10/1996 | Fleury | |

| | | | | | | |
|---|---|---|---|---|---|---|
| 5,616,138 | A | 4/1997 | Propp | 6,409,971 B1 | 6/2002 | Wilkinson et al. |
| 5,662,630 | A | 9/1997 | Raynie | 6,551,292 B1 | 4/2003 | D'Acchioli et al. |
| 5,725,515 | A | 3/1998 | Propp | 6,582,379 B1 | 6/2003 | Stisen |
| 5,792,127 | A | 8/1998 | Marran | 6,635,036 B1 | 10/2003 | Tanghoej et al. |
| 5,891,051 | A | 4/1999 | Han et al. | 6,736,803 B2 | 5/2004 | Cawood |
| 5,919,146 | A | 7/1999 | Propp | 6,793,651 B1 | 9/2004 | Bennett et al. |
| 5,961,501 | A | 10/1999 | Cassidy et al. | D496,993 S | 10/2004 | Kubalak et al. |
| 5,989,234 | A | 11/1999 | Valerio et al. | D497,205 S | 10/2004 | Kubalak et al. |
| 6,129,684 | A | 10/2000 | Sippel et al. | | | |
| 6,129,714 | A | 10/2000 | Kocsi | | | |
| 6,132,407 | A | 10/2000 | Genese et al. | | | |
| 6,210,383 | B1 | 4/2001 | Want et al. | | | |
| 6,250,482 | B1 | 6/2001 | Want et al. | | | |
| 6,338,728 | B1 | 1/2002 | Valerio | | | |
| 6,409,131 | B1 | 6/2002 | Bentley et al. | | | |

FOREIGN PATENT DOCUMENTS

| | | |
|---|---|---|
| GB | 1 128 186 A | 9/1968 |
| GB | 2 322 079 | 8/1998 |
| WO | WO 85/05550 A | 12/1985 |

\* cited by examiner

URINE METER WITH IMPROVED DRAIN CONSTRUCTION

BACKGROUND

1. Technical Field

The present disclosure relates to a urine meter for use with a urine collection bag or system. More specifically, the present disclosure relates to a urine meter constructed to facilitate faster drainage and more precise volume measurement.

2. Background of Related Art

Urine meters are well known and are commonly used in conjunction with urine collection systems for catheterized patients. Typically, a urine meter is secured to a urine collection bag and receives urine from a supply tube which is connected to a catheterized patient. The urine meter has a limited volume and includes indicia for measuring the volume of fluid deposited therein. The urine meter is attached to a urine collection bag of greater volume and includes at least one drain opening positioned in an upper portion of the meter which is in fluid communication with the urine collection bag. After a predetermined period of time of use, the volume of urine in the urine meter can be recorded and the contents of the urine meter can be emptied into the urine collection bag.

Generally, a urine meter is attached directly to a urine collection bag and can be emptied into the urine collecting bag by tilting the urine meter such that the urine in the urine meter flows from a bottom portion of the urine meter to an upper portion of the meter into communication with the drain opening. Because of the construction of known urine meters and the positioning of the drain opening, emptying of the urine meter may be time consuming and not completely effective, i.e., small volumes of fluid may remain in the meter. Further, current urine meter configurations make it difficult to accurately measure small volumes of urine within the meter.

In known urine meters, a sample of urine can be taken for testing from the urine meter from a drain port via a valve member. The valve can be opened to allow urine to flow from the meter into a receptacle. Although the provision of such a drain port facilitates testing of urine which is relatively fresh, i.e., has not been contaminated by contaminants located within the urine collection bag, the use of a drain port can be difficult to use with a single hand and expose medical personnel to urine.

Accordingly, it would be desirable to provide a urine meter which is constructed to drain into a urine collection bag more quickly and completely. It would also be desirable to provide a urine meter which can more accurately indicate the volume of fluid within the urine meter. Finally, it would be desirable to provide a urine meter which facilitates contact-free removal of urine samples from the urine meter without contaminating the urine sample or contaminating urine within the urine meter.

SUMMARY

In accordance with the present disclosure, a urine meter is provided which includes a housing and a substantially transparent faceplate. The housing defines an inlet port and includes an upper wall, a lower wall, sidewalls, and a rear wall. In one embodiment, the upper wall of the housing is substantially concave and includes a central portion and first and second ends. The central portion has a height which is less than the height of the first and second ends of the upper wall. The housing also defines at least one drain opening. In one embodiment, first and second drain openings are provided. The first and second drain openings are positioned adjacent the first and second ends of the upper wall. In one embodiment, a recessed channel is formed at least partially about the first and second drain openings.

In one embodiment, the at least one fluid receptacle includes first and second receptacles. The first fluid receptacle is centrally located within the housing to receive fluid from the inlet port. The second fluid receptacle includes a left receptacle portion positioned on one side of the first receptacle and a right receptacle portion positioned on an opposite side of the first receptacle. The left and right receptacle portions are interconnected by a fluid channel. In one embodiment, the fluid channel extends beneath the first receptacle.

The urine meter can include a drain tube having a discharge end which extends or is positioned through the inlet port. The drain tube includes a smooth internal surface having substantially no discontinuities. In one embodiment, the discharge end of the drain tube is angled or tapered.

In one embodiment, a needleless sampling port is provided to access fluid in the first receptacle. The sampling port can be supported on the faceplate such that upon attachment of the faceplate to the housing, the sampling port is in fluid communication with the first receptacle.

The faceplate can include indicia for identifying the volume of fluid within the first and second fluid receptacles. One or more sets of indicia may be provided to indicate the volume of fluid in each or all of the housing receptacles.

BRIEF DESCRIPTION OF DRAWINGS

Various embodiments of the presently disclosed urine meter are disclosed herein with reference to the drawings, wherein.

DETAILED DESCRIPTION OF EMBODIMENTS

Embodiments of the presently disclosed urine meter will now be described in detail with reference to the drawings wherein like reference numerals designate identical or corresponding elements in each of the several views.

FIGS. 1-5 illustrate one embodiment of the presently disclosed urine meter which is shown generally as 10. Urine meter 10 includes a housing 12 and a faceplate 14. Housing 12 and faceplate 14 can be constructed from a polyester terephalate modified with glycol or PETG material which is a rigid substantially transparent material. Alternately, other materials having similar characteristics can be used to construct housing 12 and faceplate 14. In one embodiment, housing 12 has a width which is greater than its height and defines a first receptacle 16 and a second receptacle 18. First receptacle 16 is centrally located within housing 12 and is dimensioned and configured to receive small volumes of urine. As illustrated, first receptacle 16 may be dimensioned to receive about 45m1 of fluid. Alternately, the dimensions of first receptacle 16 may be varied to hold different volumes of fluid, e.g., 10-100 ml. In one embodiment, first receptacle 16 is defined by a substantially U-shaped wall 20 which can be formed integrally or monolithically with housing 12. Alternately, other wall or receptacle configurations are envisioned, e.g., rectangular, etc. The upper end of receptacle 16 defines an opening 22 dimensioned to receive fluid flow, as will be discussed in further detail below, and allow fluid to spillover from first receptacle 16 into second receptacle 18.

Second receptacle 18 is positioned about first receptacle 16 and includes a left receptacle portion 18a and a right receptacle portion 18b. Left and right receptacle portions 18a and 18b communicate with each other via a fluid channel 24 extending beneath first receptacle 16. Fluid channel 24 allows the pressure and thus the level of fluid in receptacle portions 18a and 18b to become balanced even though a greater volume of fluid may spillover from first receptacle 16 into one or the other of the left and right receptacle portions 18a and 18b.

Figure 8:
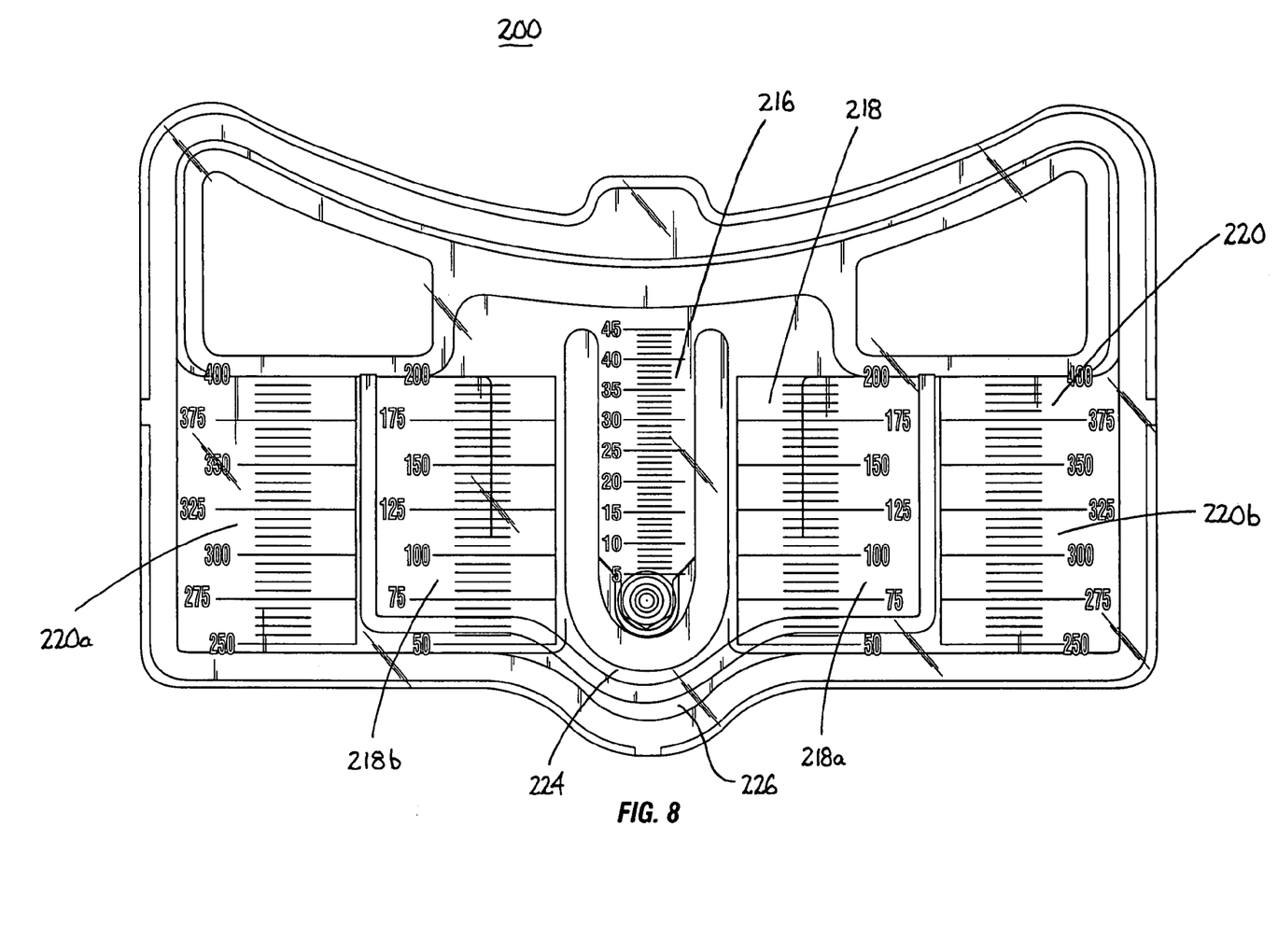
FIG. 8 is a front view of another embodiment of the presently disclosed urine meter.

In an alternate embodiment of the presently disclosed urine meter shown in FIG. 8, urine meter 200 includes a first receptacle 216, a second receptacle 218 and a third receptacle 220. Second receptacle 218 includes receptacle portions 218a and 218b which are interconnected by a fluid channel 224. Third receptacle 220 includes receptacle portions 220a and 220b which are interconnected by a fluid channel 226. The receptacles 216, 218 and 220 are positioned such that fluid will first fill up first receptacle 216 and then cascade into second receptacle 218. When second receptacle 218 is full, fluid will cascade into the third receptacle 220. Channels 224 and 226 allow the level of fluid in receptacle portions 218a and 218b and 220a and 220b to become balanced or level as discussed above. By providing a third receptacle positioned about the second receptacle, greater spacing can be provided between indices 230 of meter 210 to allow more accurate measurement of the volume of fluid within the meter.

Figure 1:
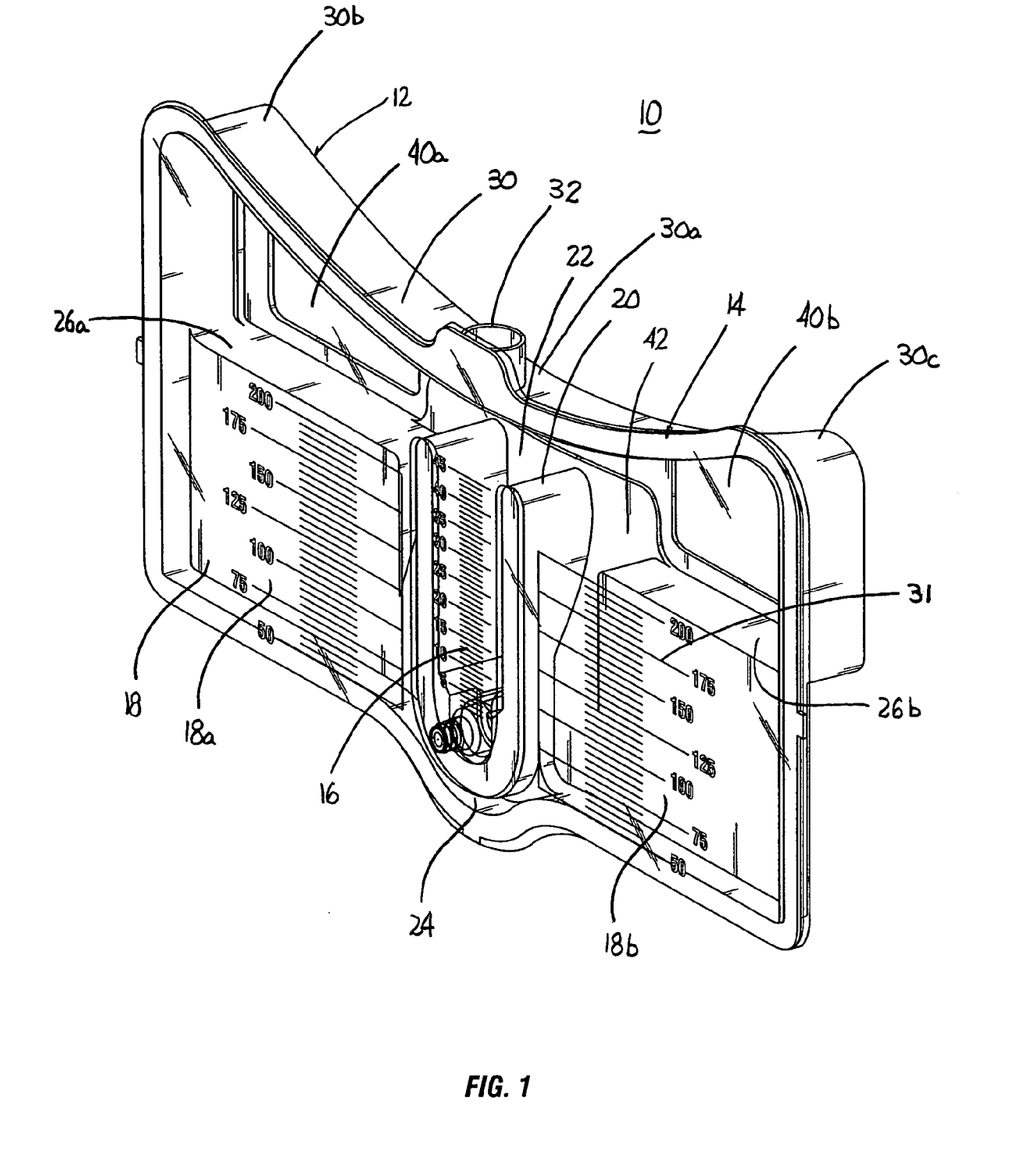
FIG. 1 is a front perspective view of one embodiment of the presently disclosed urine meter.
Figure 1A:
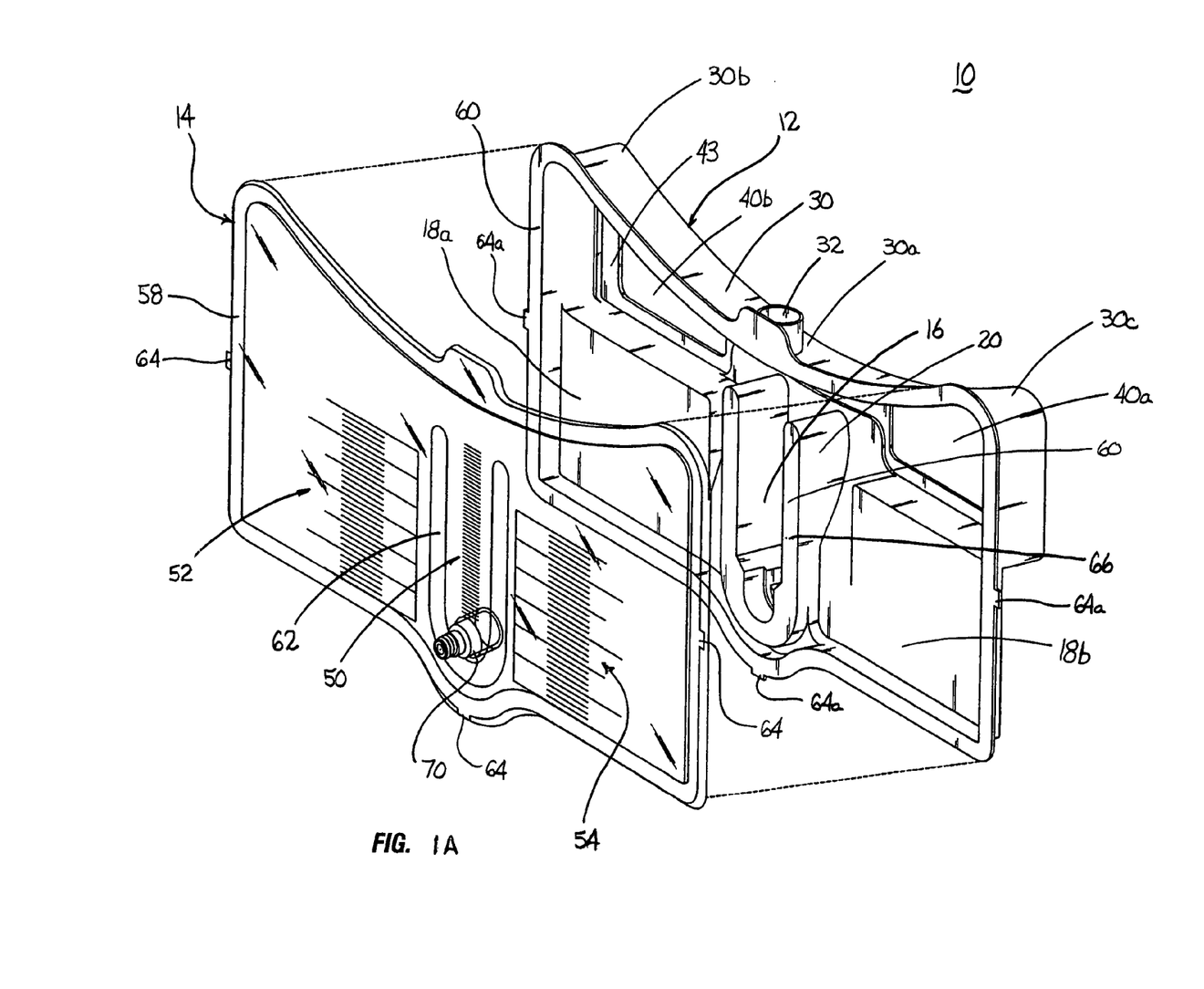
FIG. 1A is a front perspective view of the urine meter shown in FIG. 1 with parts separated.
Figure 2:
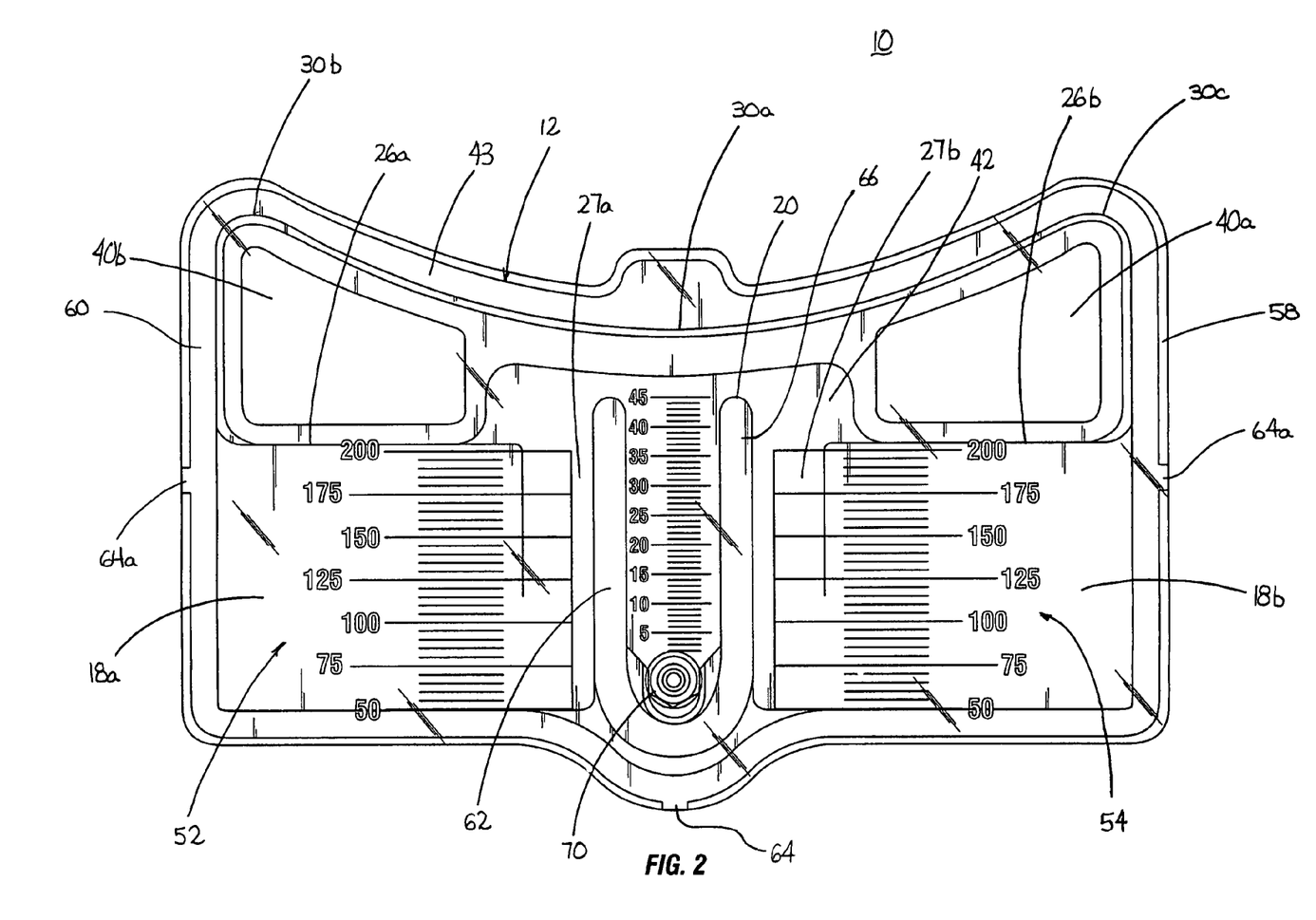
FIG. 2 is a front view of the urine meter shown in FIG. 1.

Housing 12 includes a stepped portions 26a and 26b which define the rear walls of left and right receptacle portions 18a and 18b, respectively. Stepped portions 26a and 26b are positioned adjacent indicia on faceplate A and reduce the depth of receptacle portions 18a and 18b within housing 12 to thereby reduce the volume of receptacle portions 18a and 18b. By reducing the volume of receptacle portions 18a and 18b in this manner in conjunction with providing a second receptacle 18 positioned about a centrally located first receptacle 16, smaller volumes of fluid are more readily apparent in second receptacle 18. Thus, greater spacing can be provided between indicia 30 provided on faceplate 14 to allow more accurate measurement of small volumes of fluid in second receptacle 18.

In one embodiment, housing 12 also defines sloped or angled surfaces 27a and 27b positioned between stepped portions 26a and 26b, respectively and opposite sides of wall 20. Sloped surfaces 27a and 27b define a sloped surface which extends from a front face of stepped portions 26a and 26b, respectively, towards a rear wall 42 of housing 12. Sloped surfaces 27a and 27b allow fluid to flow from receptacle portions 18a and 18b towards drain openings 40a and 40b as will be discussed in further detail below.

The upper portion of housing 12 is defined by an upper wall 30 having a substantially concave configuration. Upper wall 30 has a central portion 30a defining a low point of the concavity and opposite ends 30b and 30c which are positioned above central portion 30a (FIG. 1A). An inlet port 32 which can be integrally or monolithically formed with housing 12 extends through central portion 30a of upper wall 30. Inlet port 32 is positioned to enter urine meter 10 at the lowest point of upper wall 30 to improve the flow of fluid from a patient into the urine meter, i.e., by lowering the inlet height of fluid entry into meter 10 in a gravity feed system, the differential height between the inlet and outlet ends of a drain tube is increased to increase the head pressure of the fluid. In one embodiment, upperwall 30 defines a smoothly, curved inner surface. Alternately, upper wall 30 can have a variety of different concave configurations in which a central portion of upper wall 30 defines a low point of the upper wall. For example, upper wall 30 can include a pair of linear wall portions which converge downwardly towards each other and meet at a central portion of the upper wall.

Housing 12 also defines a pair of spaced drain openings 40a and 40b which are positioned above receptacle portions 18a and 18b, respectively. Drain openings 40a and 40b are defined in opposite sides of a rear wall 42 of housing 12 and are located beneath ends 30b and 30c of upper wall 30 of housing 12 such that openings 40a and 40b extend to a position adjacent the upper most portions of housing 12. A recessed channel or groove 43 is positioned around drain openings 40a, along upper wall 30 and around drain opening 40b. Groove 43 functions enhance drainage of urine meter 10. In one embodiment, drain openings 40a 40b each define a substantial portion of an upper portion of the overall surface area of an upper portion of rear wall 42 of housing 12. Because of the area of openings 40a and 40b, their location in the uppermost corner of the concave upper wall 30, the provision of a groove about drain openings 40a and 40b, and sloped walls 27a and 27b, fluid can be emptied from urine meter quickly and completely. It is envisioned that any one or any combination of these features can be incorporated into a urine meter to improve drainage of the urine meter.

Referring to FIG. 1A, faceplate 14 is substantially transparent and includes a first set of indicia 50 positioned adjacent first receptacle 16, a second set of indicia 52 positioned adjacent first receptacle portion 18a and a third set of indicia 54 positioned adjacent second receptacle portion 18b. Indicia 52 is substantially identical to indicia 54. Faceplate 14 includes an outer rim 58 which is positioned to abut an outer rim 60 positioned about a forward portion of housing 12. Rims 58 and 60 are secured together in a fluid tight manner to seal faceplate 14 to housing 12. In one embodiment, faceplate 14 is secured to housing 12 using radio frequency ("RF") welding. Alternately, other known fastening techniques can be used to secure faceplate 14 to housing 12, e.g., adhesives, clamps, screws, ultrasonic welding, etc. A central portion of faceplate 14 includes a seal portion 62 which is configured to abut a face 66 of wall 20 defining first receptacle 16. Seal portion 62 is secured to wall 20 in a fluid tight manner, e.g., welding, adhesives, etc. to seal first receptacle 16 from second receptacle 18. A series of positioning tabs 64 are positioned about faceplate 14. Positioning tabs 63 align with tabs or slots 64a formed on housing 12 to properly position faceplate 14 in relation to housing 12 during attachment of faceplate 14 to housing 12.

Faceplate 14 also includes a sampling port 70 which is positioned to provide access to fluid in the bottom of receptacle 16. Sampling port 70 is configured to access first receptacle 16 using either a luer-loc or slip tip syringe. Such a sampling port is available from NP Medical, Inc., a division of Nypro, Inc., of Clinton, Mass. Sampling port 70 eliminates a potential site for bacterial entrance into urine meter 10, while decreasing the likelihood of human contact with urine.

Figure 5:
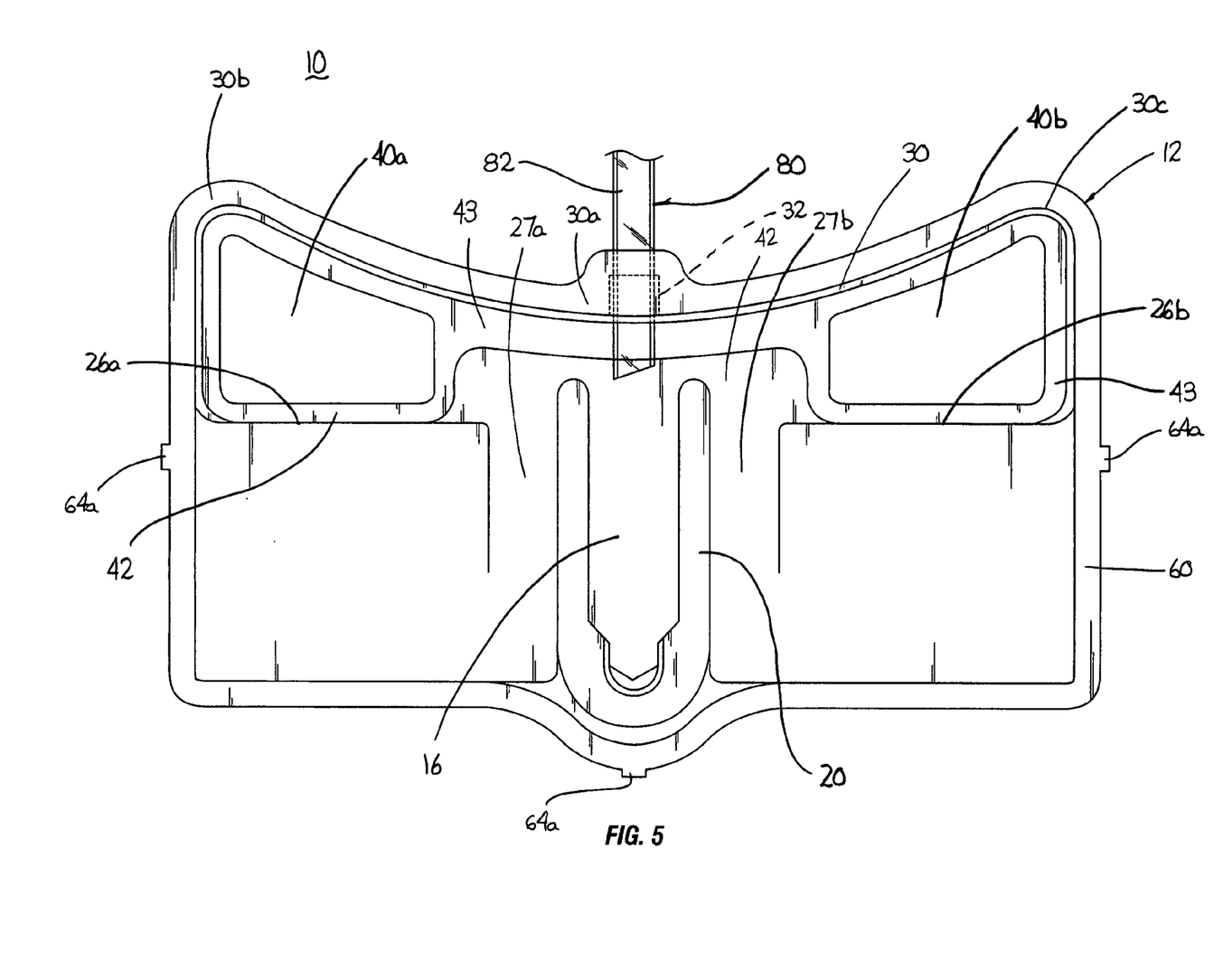
FIG. 5 is a front view of the housing of the urine meter shown in FIG. 1 with the urine meter inlet port shown in phantom and a drain tube positioned through the inlet port.

Referring to FIG. 5, as discussed above, inlet port 32 is dimensioned to receive the second end 82 of a drain tube 80. The first end of tube 80 (not shown) is adapted to be in fluid communication with a catheterized patient such that urine from a patient's bladder flows from the patient's bladder and is initially collected in urine meter 10. As illustrated in FIG. 5, the second end 82 of drain tube 80 extends directly through inlet port 32 to a position above first receptacle 16. The inner wall of drain tube 82 defines a continuous surface having substantially no surface irregularities or breaks and is positioned to deposit fluid directly into first receptacle 16. In one embodiment, second end or discharge end 82 of drain tube 80 is angled or tapered. It has been discovered that any internal breaks or discontinuities in a drain tube or along the flow path may effect the formation of a meniscus or bubble within the drain tube. It has also been discovered that, once formed, a substantial amount of fluid or head is required to overcome the meniscus to reinitiate urine flow through the drain line. Thus, when a meniscus is formed within a drain tube, a substantial amount of urine can be trapped in the drain tube. As such, the volume of fluid collected in the urine meter will not reflect the amount of urine expelled by the patient. By providing drain tube 80 which passes directly into urine meter 10 with no surface breaks, the creation of a meniscus in the drain tube can be substantially avoided and a more accurate urine output measurement can be obtained.

Figure 3:
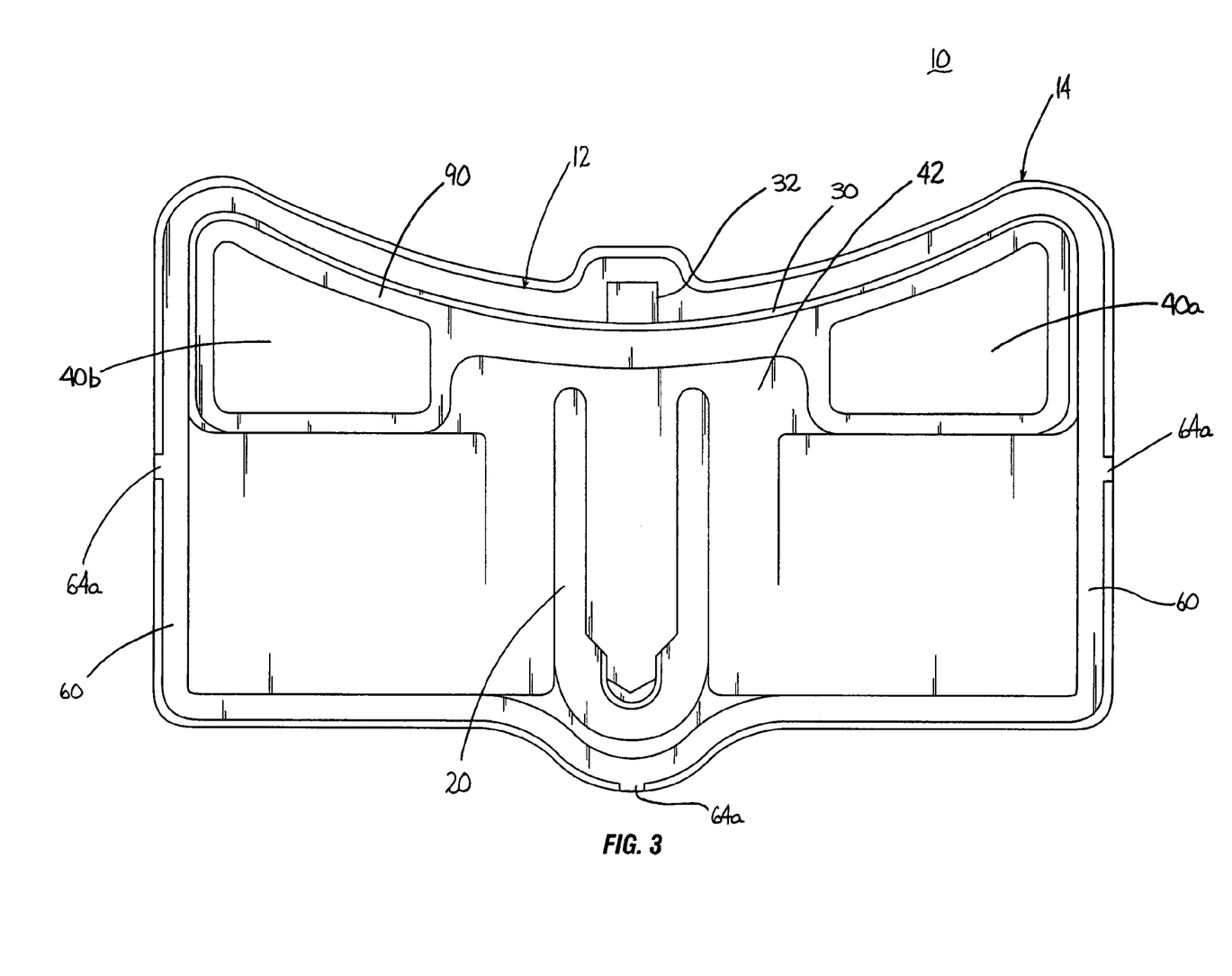
FIG. 3 is a rear view of the housing of the urine meter shown in FIG. 1.
Figure 4:
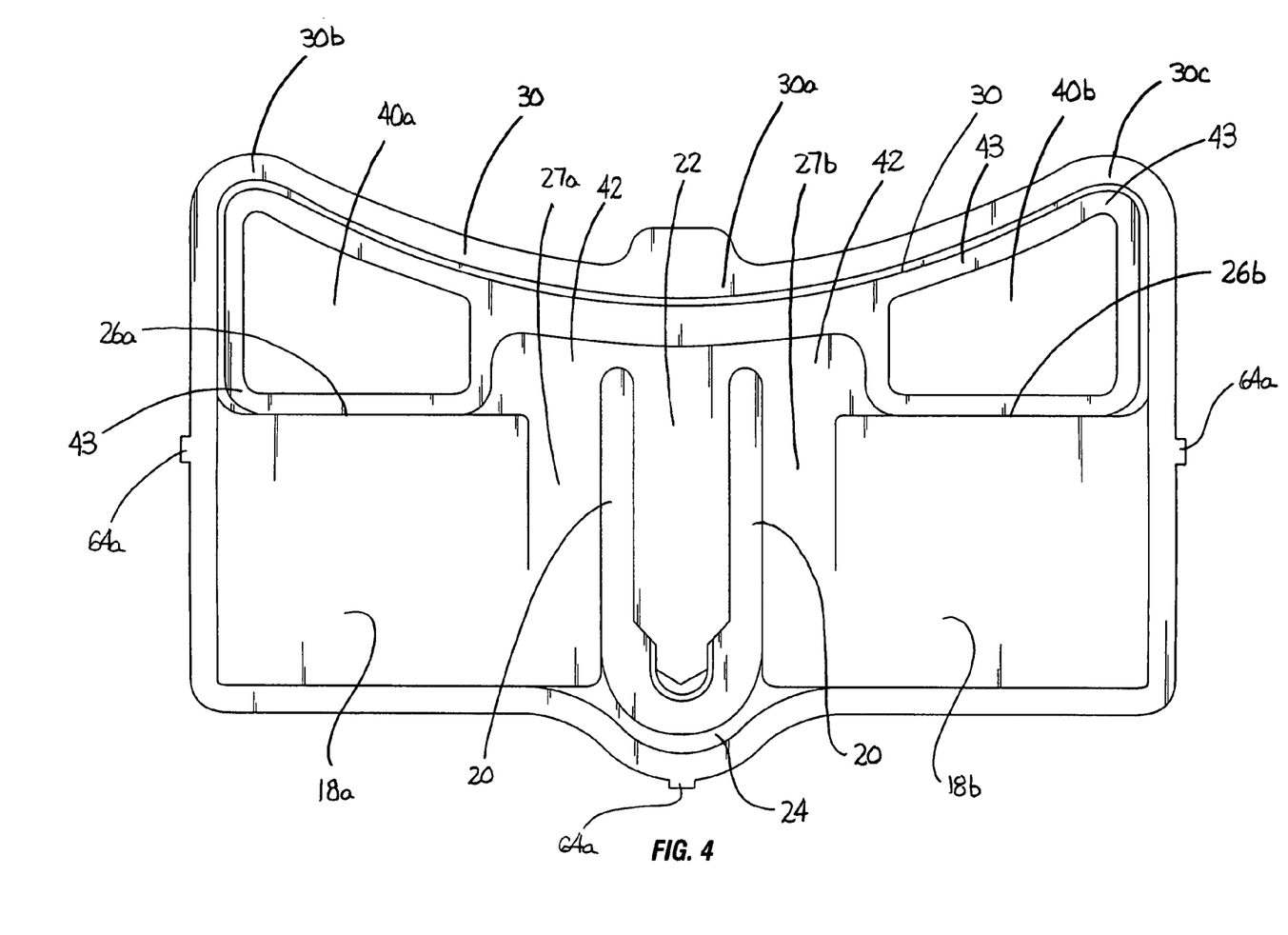
FIG. 4 is a front view of the housing of the urine meter shown in FIG. 1.

Referring to FIG. 3, housing 12 of urine meter 10 includes a raised surface 90 which extends about drain openings 40a and 40b and along rear wall 42 adjacent upper wall 30. Raised surface 90 is positioned to engage a urine collection bag 100 (FIG. 6) and be sealed in a fluid tight manner thereto.

Figure 6:
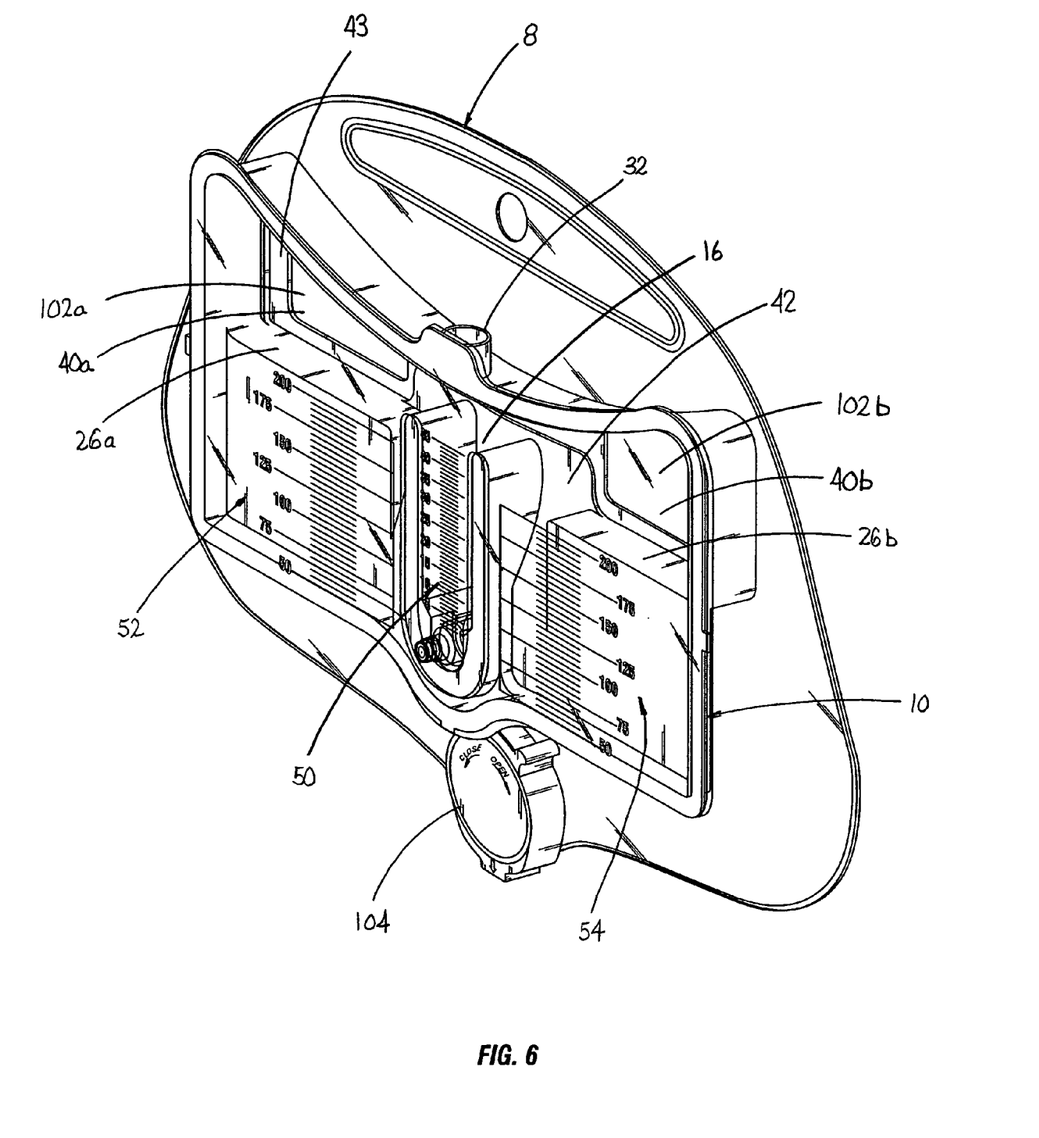
FIG. 6 is a front perspective view of the urine meter shown in FIG. 1 attached to a urine collection bag.
Figure 7:
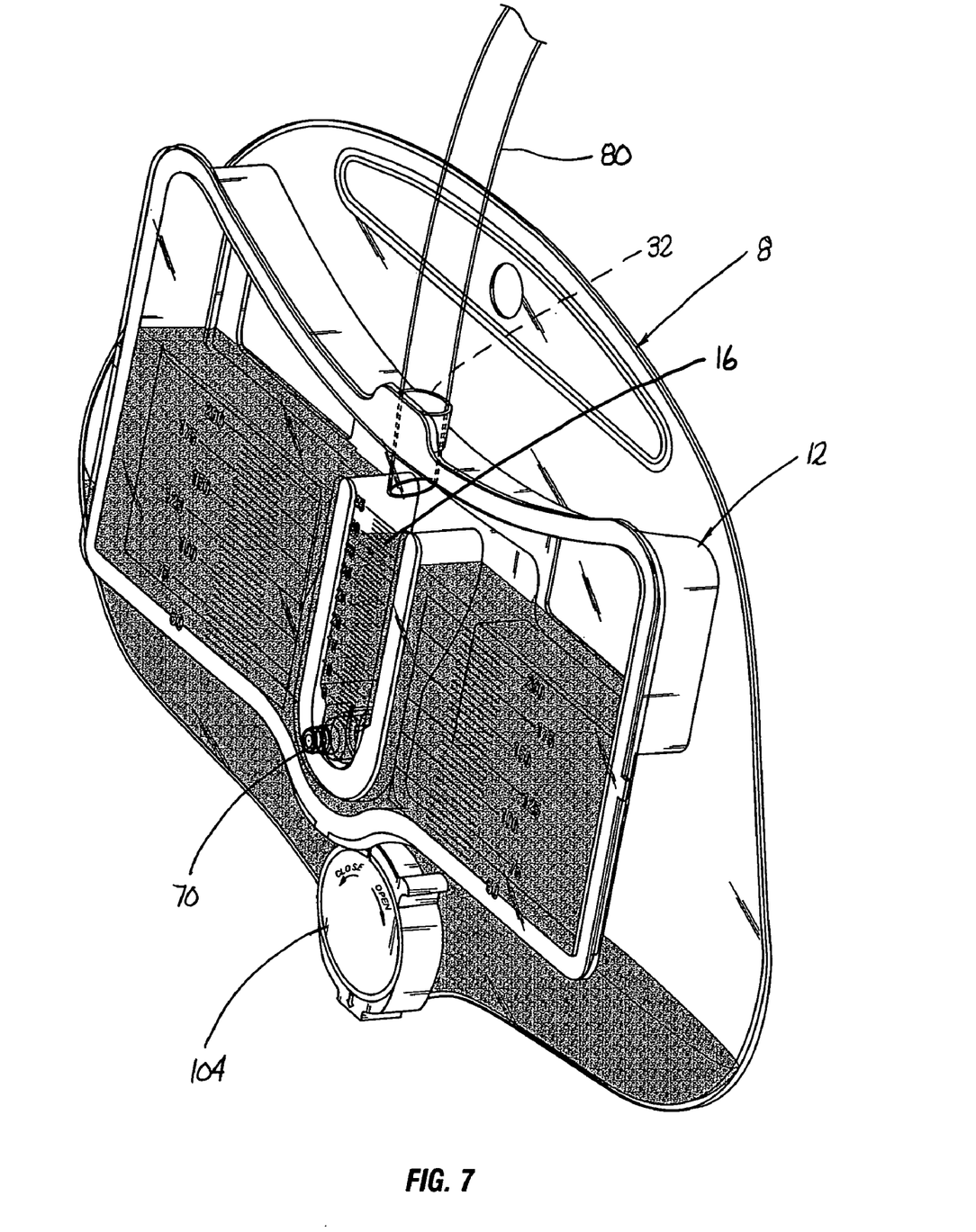
FIG. 7 is a front perspective view of the urine meter and urine collection bag assembly partially filled with urine.

Referring also to FIGS. 6 and 7, collection bag 100 includes openings 102a and 102b which register with drain openings 40a and 40b of urine meter 10. In use, urine will flow from drain tube 80 (FIG. 7) into first receptacle 16. When receptacle 16 becomes full, additional urine supplied to meter 10 through drain tube 80 will spill over into receptacle 18. When the level of fluid in urine meter 10 rises too high or urine meter 10 is tilted upwardly, urine will empty from receptacles 16 and 18, through drain openings 40a and 40b and openings 102a and 102b into collection bag 100. Collection bag 100 includes a drain valve 104 to facilitate drainage of collection bag 100.

It will be understood that various modifications may be made to the embodiments disclosed herein. For example, additional walls or barriers may be provided to divide meter 10 into additional receptacles, e.g., three or more receptacles may be provided by providing an additional wall or walls in left and right receptacle portions 18a and 18b. Therefore, the above description should not be construed as limiting, but merely as exemplifications of disclosed embodiments. Those skilled in the art will envision other modifications within the scope and spirit of the claims appended hereto.

What is claimed is:

1. A urine meter comprising:
  a housing having an inlet port, the housing including an upper wall, a lower wall, first and second sidewalls, and a rear wall defining the at least one fluid receptacle, the upper wall extending between the first and second sidewalls and having a substantially concave shape, the upper wall including a central portion and first and second ends located adjacent the first and second sidewalls, the central portion having a height which is less than the height of the first and second ends of the upper wall; and
  a substantially transparent faceplate enclosing the housing, the faceplate having indicia formed thereon for identifying the volume of fluid contained within the at least one fluid receptacle;
  wherein the inlet port defines an opening extending through the central portion of the upper wall and the housing defines a first drain opening positioned adjacent the first end of the upper wall and a second drain opening positioned adjacent the second end of the upper wall, the first and second drain openings being positioned at an upper end of the fluid receptacle.

2. A urine meter according to claim 1, wherein the at least one fluid receptacle includes first and second fluid receptacles.

3. A urine meter according to claim 2, wherein the first fluid receptacle is centrally located within the housing in a position to receive fluid supplied to the urine meter through the inlet port.

4. A urine meter according to claim 3, wherein the second fluid receptacle includes a left receptacle portion and a right receptacle portion positioned on opposite sides of the first receptacle, the left and right receptacle portions being interconnected by a fluid channel extending beneath the first receptacle.

5. A urine meter according to claim 1, wherein the housing further defines at least one stepped portion positioned beneath the first and second drain openings adjacent the indicia on the faceplate, the at least one stepped portion reducing the volume of the at least one fluid receptacle to facilitate more accurate measurement of smaller volumes of fluid within the at least one fluid receptacle.

6. A urine meter according to claim 5, wherein the housing further defines at least one sloped surface extending from the at least one stepped portion towards the rear wall of the housing and the first and/or second drain opening.

7. A urine meter according to claim 6, wherein the housing further defines a recessed channel positioned at least partially about the first and second drain openings.

8. A urine meter according to claim 1, wherein the housing defines a recessed channel positioned at least partially about the at least one drain opening.

9. A urine meter according to claim 1, wherein the housing has a width which is greater than its height.

10. A urine meter according to claim 1, further including a drain tube extending through the inlet port and having a discharge end positioned within the urine meter adjacent the at least one fluid receptacle, the drain tube having an internal surface which is continuous and is absent any discontinuities, wherein the drain tube is positioned to direct fluid directly into the at least one fluid receptacle.

11. A urine meter according to claim 10, wherein the discharge end of the drain tube is angled.

12. A urine meter comprising:
  a housing defining an inlet port, at least one fluid receptacle and first and second drain openings positioned in an upper portion of the at least one fluid receptacle, the housing including an upper wall, a lower wall, first and second sidewalls, and a rear wall defining the at least one fluid receptacle, the upper wall extending between the first and second sidewalls and having a substantially concave shape, the upper wall including a central portion and first and second ends located adjacent the first and second sidewalls, the central portion having a height which is less than the height of the first and second ends of the upper wall; and
  a drain tube having a discharge end, the drain tube extending through the inlet port and having an internal surface which is continuous and substantially absent any discontinuities, the discharge end being positioned to direct fluid directly into the at least one fluid receptacle;

wherein the inlet port defines an opening extending through the central portion of the upper wall and the first drain opening is positioned adjacent the first end of the upper wall and the second drain opening is positioned adjacent the second end of the upper wall.

13. A urine meter according to claim 12, wherein the discharge end of the drain tube is angled.

14. A urine meter according to claim 12, further including a recessed channel positioned about the first and second drain openings.

\* \* \* \* \*